United States Patent [19]

Mori

[11] Patent Number: 4,970,054
[45] Date of Patent: Nov. 13, 1990

[54] BIOASSAYING DEVICE USED WITH LIGHT RADIATION

[76] Inventor: Kei Mori, 3-16-3-501, Kaminoge, Setagaya-ku, Tokyo, Japan

[21] Appl. No.: 405,801

[22] Filed: Sep. 11, 1989

[30] Foreign Application Priority Data

Nov. 24, 1988 [JP] Japan .................................. 63-297075

[51] Int. Cl.[5] ...................... G01N 21/00; G01N 21/01; G01N 21/25
[52] U.S. Cl. .................................... 422/108; 128/633; 128/665; 128/743; 356/406; 356/407; 422/82.05; 422/82.06; 422/82.12; 436/164
[58] Field of Search .................. 422/55, 58, 63, 64, 422/65, 66, 68, 108, 82.05, 82.06, 82.12; 436/164, 805; 356/73, 405, 406, 407; 128/665, 743, 633

[56] References Cited

U.S. PATENT DOCUMENTS

| | | | |
|---|---|---|---|
| 3,525,572 | 8/1970 | Hunter et al. | 356/405 |
| 3,552,852 | 1/1971 | Stemke et al. | 356/405 |
| 3,919,530 | 11/1975 | Cheng | 436/164 |
| 3,936,189 | 2/1976 | DeRemigis | 356/405 |
| 4,175,859 | 11/1979 | Hashizume et al. | 422/68 |
| 4,570,638 | 2/1986 | Stoddart et al. | 128/665 |
| 4,606,351 | 8/1986 | Lübbers | 128/665 |
| 4,737,464 | 4/1988 | McConnell et al. | 436/164 |

FOREIGN PATENT DOCUMENTS 0044609 2/1987 Japan .................................. 356/406

Primary Examiner—Robert J. Warden
Assistant Examiner—Kimberly A. Trautman
Attorney, Agent, or Firm—Jordan and Hamburg

[57] ABSTRACT

A bioassaying device for carrying out an experiment with a subject placed under a transparent portion of a base plate. The subject is irradiated with light rays emitted from light-emitting ends of three fiber optic cables. One of the three fiber optic cables radiates light rays containing plenty of the red color-spectrum component, another cable radiates the blue component and the remaining cable radiates the green component. Each of the fiber optic cables is provided with a mechanism for adjusting its inclination angle simultaneously with vertical movement of a moving plate upon which the fiber optic cables are mounted.

5 Claims, 4 Drawing Sheets

BIOASSAYING DEVICE USED WITH LIGHT RADIATION

BACKGROUND OF THE INVENTION

The present invention relates to a bioassaying device for experimenting with living organisms by exposing them to visible light rays.

The present applicant has previously proposed focusing solar rays or artificial light rays by using lenses or the like to guide the focused light rays into a fiber optic cable and to transmit them to any place where the light is needed for illumination or for other purposes as for example, to cultivate plants, chlorella, fish or the like. In the process of doing research, it has been found that visible light not containing ultraviolet and infrared rays is effective not only to promote the health of persons and prevent people's skin from aging by stimulating the body's life functions but also to noticeably aid in healing gout, neuralgia, bedsores, rheumatism, burn scars, skin diseases, bone fracture scars and so on and in relieving the pain from such diseases.

Furthermore, on the basis of the above-mentioned inventor's discovery, the applicant has previously proposed a light radiating device for radiating visible light containing none of the harmful ultraviolet and infrared rays with the aim of using it for healing various kinds of diseases, for giving beauty treatments and for promoting health. This device is intended to irradiate the patient's skin-surface with the visible-spectrum components of sunlight or artificial light transmitted through a fiber optic cable. The device ensures the safe healing of a disease by means of the light filtered of its infrared and ultraviolet rays which are known to be harmful to people. In order to increase the healing effect of the light radiation provided by the device, it is also necessary to vary such conditions as the amount of light, the wavelength components, the light's intensity etc. Furthermore, synergism (i.e. the combined effect) of medication and light radiation must be studied by using laboratory animals such as rabbits, mice etc.

SUMMARY OF THE INVENTION

It is an object of the present invention to provide a bioassaying device for experimenting with living organisms by exposing them to visible light rays.

It is another object of the present invention to provide a bioassaying device with visible light radiation making it possible to carry out more effectively experiments with living organisms in relation to the effects of the visible light's radiation.

It is another object of the present invention to provide a bioassaying device with visible light radiation, which is capable of irradiating the living subject with light by changing its energy intensity and/or color temperature or operating at fixed values of energy intensity and/or color temperature.

DESCRIPTION OF THE PREFERRED EMBODIMENTS

Figure 1:
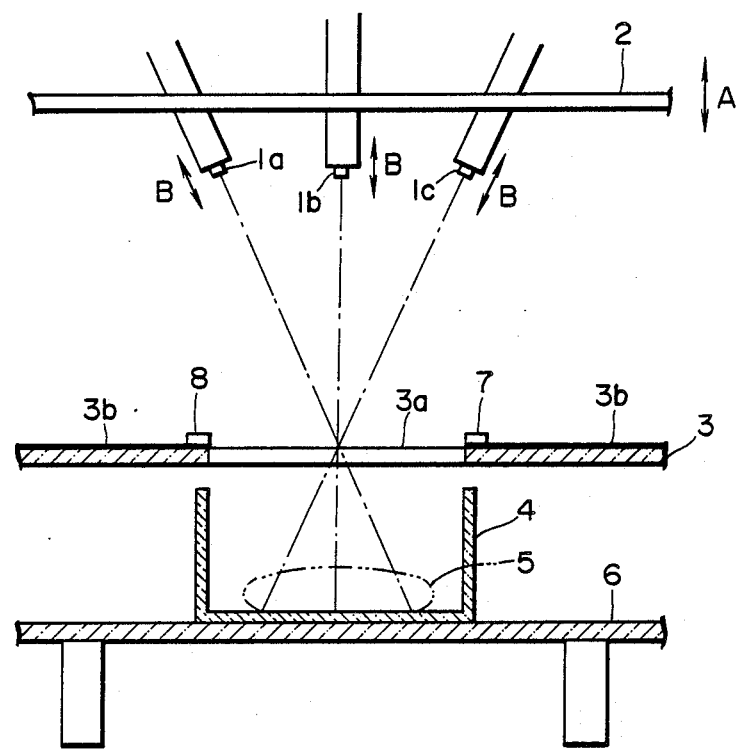
FIG. 1 is a view for basically explaining the bioassaying device according to the present invention.

FIG. 1 is a construction view showing the workings of a bioassaying device according to the present invention. In FIG. 1, numerals 1a–1c designate fiber optic cables for transmitting solar rays or artificial light rays containing much of the red color component (for instance, by the cable 1a), the blue color component (by the cable 1b) and the green color component (by the cable 1c). However, the infrared and ultraviolet rays have been filtered out because they are known to be harmful to living organisms. Element 2 is a moving plate which supports said fiber optic cable and can move in the direction of the arrows A, and 3 is a transparent element which has a transparent or hollow center portion 3a and a peripheral portion 3b preferably formed as a reflecting surface eliminating the possibility of heat transmission therethrough to a subject being exposed to light radiation. Element 4 is a laboratory dish, 5 is a subject (living organism) placed in laboratory dish 4, and 6 is a base plate for placing thereon laboratory dish 4. The laboratory dish may be omitted in case the subject 5 does not require it to be placed therein. Accordingly, the base plate 6 is not always needed. Element 7 is a light energy sensor (illumination photometer) and 8 is a color temperature meter. The light energy sensor 7 detects the intensity of the light to be supplied to a living organism 5 in order to always keep the light radiation energy at an optimum level, while the color temperature meter 8 measures the color temperature of the light to be supplied to the living organism 5 and adjusts the wavelength components of the light so as to always maintain the optimum color temperature of the light radiation. Since every living organism 5 requires its own optimum conditions in relation to the illumination intensity and color temperature of the light radiation, in order to effectively carry out an experiment with a living organism, it is necessary to adjust the illumination intensity and the color temperature of the light to optimum values for the living organism. The illumination intensity (i.e. the light energy intensity) can be adjusted by moving the moving plate 2 in the direction indicated by the arrows A to change the distance from the light-emitting ends of all fiber optic cables to the living organism. The color temperature of the light radiation can be adjusted by individually shifting each cable's light-emitting end in the direction indicated by the arrows B to change the distance between the living organism and the light-emitting end of the fiber optic cable, i.e., to change the intensity of the light containing plenty of a specified color component.

Figure 2:
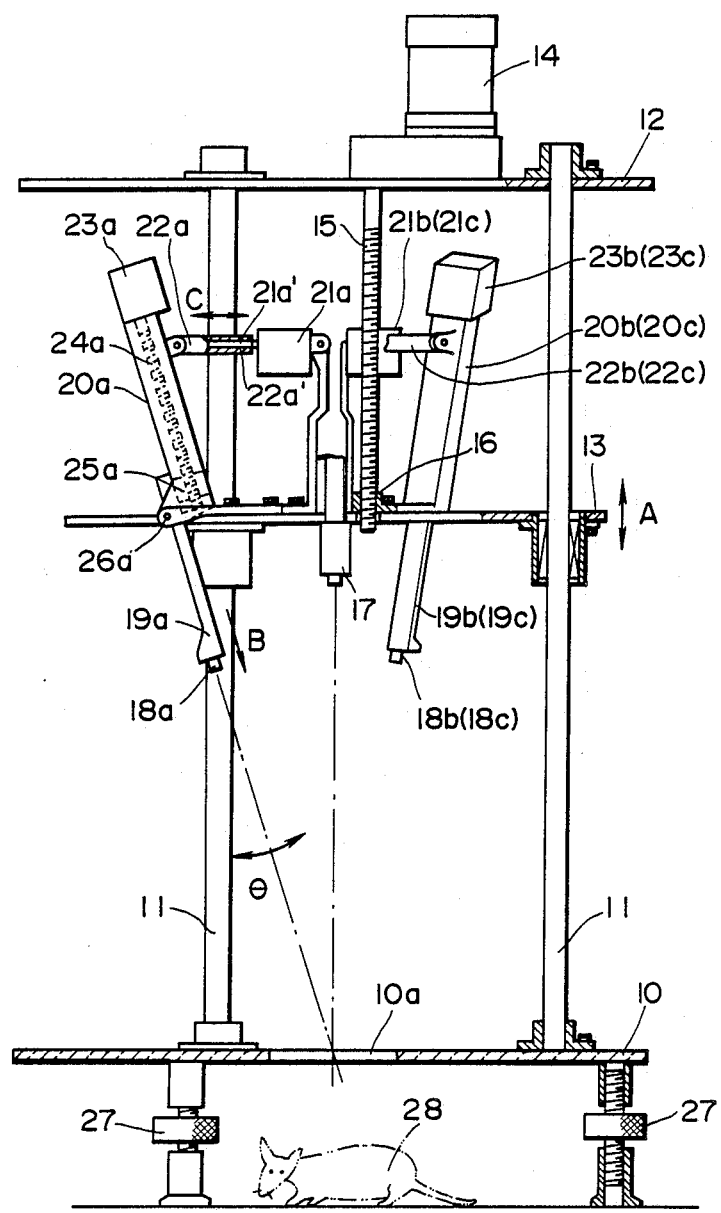
FIG. 2 is a construction view for explaining an embodiment of the bioassaying device with light radiation according to the present invention.

FIG. 2 is a view showing an embodiment of the bioassaying device, according to the present invention, capable of adjusting the illumination intensity and color temperature of the light radiation. In FIG. 2, 10 is a supporting plate (corresponding to the transparent plate 3 shown in FIG. 1), 11 are columns vertically installed on the supporting plate 10, 12 is a fixed plate supported by the upper ends of the columns 11, 13 is a moving plate capable of vertically travelling along the columns 11 (moving plate 13 corresponding to the moving plate 2 shown in FIG. 1), 14 is a motor for moving the moving plate 13 in the direction indicated by the arrows A, 15 is a feed screw to be rotated by the motor 14 and 16 is a nut threadably engaged with the feed screw and integrally fixed to the moving plate 13. When the feed screw 15 is rotated by the motor 14, the nut 16 together with the moving plate 13 moves in the direction indicated by the arrows A. Element 17 is the light-emitting end of a fiber optic cable, which is secured at the center of the moving plate 13 and 18a, 18b and 18c (18c not shown) are other fiber optic cable ends, each of which is attached to the moving plate 13 in such a way that it may move in the direction indicated by the arrows B and be rotated in the direction indicated by the arrows $\theta$. Elements 19a, 19b, 19c (19c not shown) are arms for supporting respectively the fiber optic cables 18a, 18b and 18c. Elements 20a, 20b and 20c (20c not shown) are arms for moving respectively the supporting arms 19a, 19b, 19c in the direction indicated by the arrows B and also for rotating respectively the same arms in the direction indicated by the arrows $\theta$. Elements 21a, 21b and 21c (21c not shown) are motors for rotating respectively pairs of the arms 20a, 19a;, 20b, 19b; and 20c, 19c in the direction indicated by the arrows $\theta$. Elements 22a, 22b and 22c (22c not shown) are moving arms capable of traveling in the direction indicated by the arrows C when they are driven by the motors 21a, 21b and 21c respectively. Elements 23a, 23b and 23c (23c not shown) are motors for rotating respectively the feed screws 24a, 24b and 24c (24b and 24c are not shown). Elements 25a, 25b and 25c (25b and 25c are not shown) are nuts threadably engaged with the respective feed screws 24a, 24b and 24c. The light emitted from the fiber optic cable 17, arranged at the center of the moving plate, may be, for example, such that it corresponds to white-colored sunlight. However, as described later, the fiber optic cable 17 is not always needed. The light emitted from the fiber optic cable 18a contains plenty of the red color component, the light emitted from the fiber optic cable 18b contains plenty of the blue color component and the light emitted from the fiber optic cable 18c contains plenty of the green color component. Accordingly, the total composite light may also be varied in its color, e.g. white, red, blue or green by adjusting the amount of light rays from the cables 18a, 18b and 18c. Since white light can be obtained by mixing the light rays emitted from the fiber optic cables 18a, 18b and 18c, the fiber optic cable 17 is not always needed. In this embodiment, in the state shown, the light beams from the fiber optic cables 17, 18a, 18b and 18c respectively pass through the transparent portion 10a of the supporting plate 10 and then, in the neighborhood of the subject 28, they are mixed with each other to form a composite light for irradiating the subject. The illumination intensity and the color temperature of the composite light can be preset to optimum values for the subject 28. However, whenever the subject 28 is replaced by another subject or any of the test conditions is changed, the preset values of the composite light's illumination intensity and color temperature must be readjusted. Furthermore, even in the case when the same subject is exposed to light radiation at constant levels of illumination intensity and color temperature, readjustment is also required since both parameters of the light transmitted through each fiber optic cable may be changed in a day. Also depending upon the weather, for example, the color of the sun's light becomes red in the morning and in the evening.

In FIG. 2, the light energy intensity can be adjusted by moving the moving plate 13 in the direction indicated by the arrows B by using the motor drive 14. However, since the fiber optic cables 18a, 18b and 18c are also moved up or down together with the moving plate 13, the position for forming the composite light is shifted away from the subject to be irradiated i.e., if no additional adjustment is made when the moving plate 13 is adjusted. The motors 21a, 21b and 21c and moving arms 22a, 22b and 22c are adapted to compensate for the above-mentioned cable's shifting. When the moving plate 13 is driven by the motor 14 into a vertical movement together with the fiber optic cables, the arms 22a, 22b and 22c are driven at the same time by their respective motors 21a, 21b and 21c in order to move in the direction indicated by the arrows C. The movement of each arm is performed by means of a combination of a feed screw and a fixed nut. Namely, a feed screw 21a' (21b', 21c') to be rotated by the motor 21a (21b, 21c) and a nut 22a' (22b', 22c') secured to the arm 22a (22b, 22c) were earlier engaged with each other. The arm 22a can be moved in the direction of the arrows C by the motor 21a through the above-mentioned feeding mechanism. For instance, when the moving plate 13 is moved upwards, the arm 22a is synchronously drawn towards the motor 21a. When the moving plate 13 is moved downwards, the arm 22a is synchronously pushed apart from the motor 21a. Such motions of the arm 22a (22b, 22c) are accompanied by the turning motions of the arms 24a and 19a (24b and 19b, 24c and 19c) in the direction of the arrows $\theta$ about the supporting point 26a, as a result of which the light rays from the fiber optic cables may be directed towards the subject. In other words, the light rays can be focused onto the subject without changing their color temperature. Adjustment of the color temperature of the light radiation for the subject 28 may be performed as follows: When the feeding screw 24a (24b, 24c) is rotated by the motor 23a (23b, 23c), the nut 25a (25b, 25c), which is threadably engaged with the feed screw 24a and secured to the moving plate, moves along the length of the feed screw 24a and thereby the arm 19a supporting the fiber optic cable 18a moves in the direction indicated by the arrow B so as to adjust the color temperature of the light. The light color temperature can be adjusted, for instance, close to red by putting the fiber optic cable 18a for transmitting the light containing much of the red color component closer to the subject 28 and, at the same time, by putting the other fiber optic cables 18b, 18c far from the subject 28. Namely, any desired color temperature of the light may be obtained by adjusting the distance from the subject 28 to the light-emitting ends of the fiber optic cables 18a–18c. Adjusters 27 are provided for adjusting the level of the supporting plate 10 so that the subject placed under the supporting plate 10 may be suitably exposed to the light rays. While in the case of FIG. 3 the subject to be exposed to the light radiation is an animal, it is not limited to animals and other kinds of living things such as people, plants, fish, cells and so on may be used. For instance, it is possible to perform an experiment with a subject placed in a laboratory dish (such as shown in FIG. 1) under the supporting plate 10.

Figure 3:
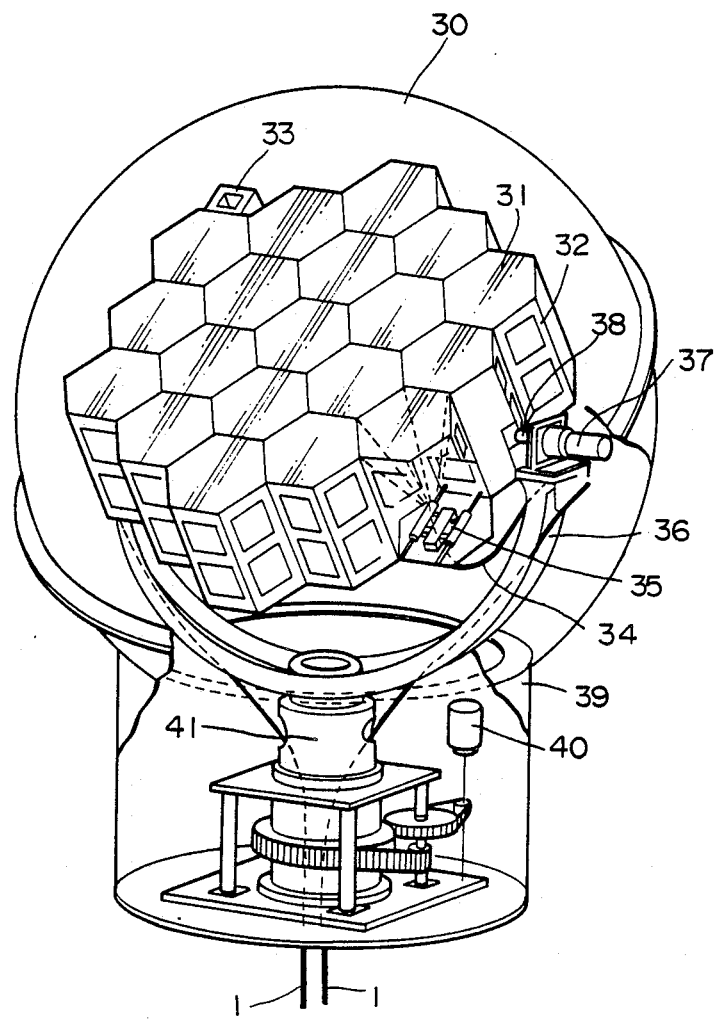
FIG. 3 is a view illustrating an embodiment of a solar ray collecting and transmitting device which can automatically collect and introduce solar rays into fiber optic cables for transmitting the same therethrough to a desired place.

FIG. 3 is a construction view for explaining, by way of example, a solar ray collecting device for guiding the sunlight into the afore-mentioned fiber optic cable. As shown in FIG. 3, the solar ray collecting device comprises a transparent protective capsule 30, Fresnel lenses 31, lens holders 32, a solar position sensor 33, fiber optic cables composed of a large number of optical fibers 34, optic cable holders 35, an arm 36, a pulse motor 37, a horizontal revolution shaft 38 to be driven by the pulse motor 37, a base 39 for supporting the protective capsule 30, a pulse motor 40 and a vertical revolution shaft 41 to be driven by the pulse motor 40.

The direction of the sun is detected by means of the solar position sensor 33 and its detection signal controls the pulse motors 37 and 40 for rotating respectively the horizontal shaft 38 and the vertical shaft 41 so as to always direct the lenses 31 toward the sun, and the sunlight focused by each lens 31 is guided into each optic fiber 34 through its end surface set at the focal point of the lens. The optical fiber 34 arranged at the respective lenses 31 are collected and bundled together as a cable 1 which is drawn from the solar ray collecting device and then is led to any desired place wherein the light rays are used for bioassaying as regards the light reaction of living organisms.

Figure 4:
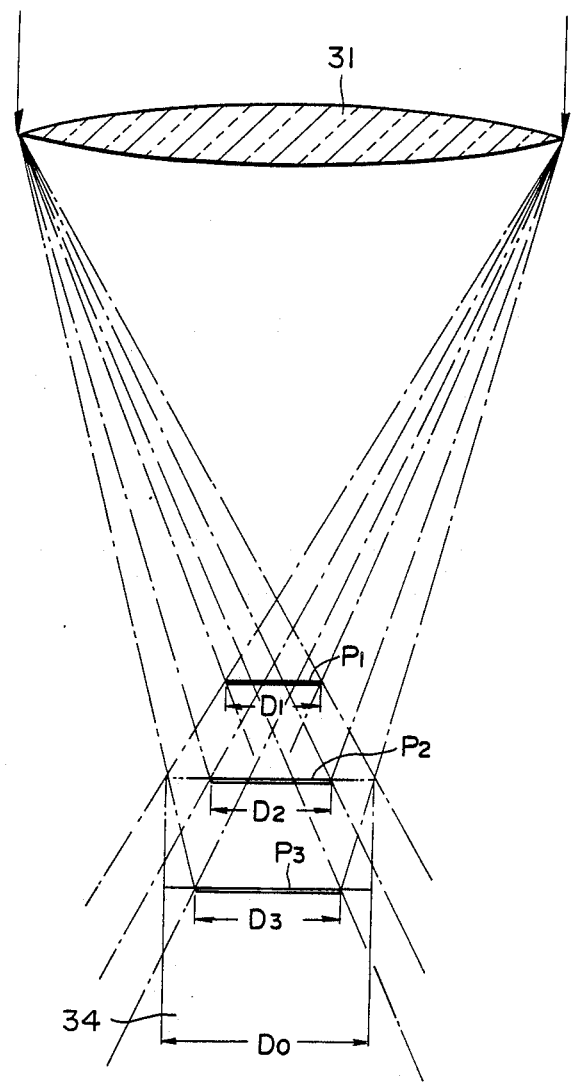
FIG. 4 is a view for basically explaining how to guide a desired color component of light into a fiber optic cable.
Figure 5:
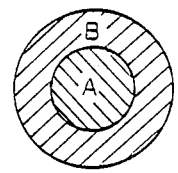
FIG. 5 is a view showing an example of a solar image focused through a lens.

FIG. 4 is a view for explaining how to guide the solar rays into an optical fiber. In FIG. 5, 31 is a Fresnel lens or the like and 34 is an optical fiber for receiving the solar rays focused by the lens 31 and transmitting the same therethrough to any desired place where the light is needed. When focusing the sunlight through the lens system, the solar image, as shown in FIG. 5, has a central portion A consisting of almost white light and a circumferential portion B containing therein a large amount of the light components having wavelengths corresponding to the focal point of the lens system. Namely, when focusing sunlight through the lens system, the focal point and the size of the solar image will vary in accordance with the component wavelengths of the light. For instance, the blue color light having a short wavelength makes a solar image of diameter D1 at position P1. Furthermore, the green color light makes a solar image of diameter D2 at position P2 and the red color light makes a solar image of diameter D3 at position P3. Consequently, as shown in FIG. 4, when the light-receiving end-surface of the optical fiber is set at the position P1, it is possible to collect the sunlight containing much of the blue color component at the circumferential portion thereof. When the light-receiving end-surface of the optical fiber is set at the position P2, it is possible to collect the sunlight containing much of the green color component at the circumferential portion thereof. When the light-receiving end-surface of the optical fiber is set at the position P3, it is possible to collect the sunlight containing plenty of the red color component at the circumferential portion thereof. In each case, the diameter of the optical fiber can be selected in accordance with the light components to be collected. For instance, the required diameters of fiber optic cables are D1, D2 and D3, respectively, depending on the colors of the light rays to be stressed, i.e. the blue, green and red colors. In such a way, the required amount of the fiber optic cable can be saved and thereby the sunlight containing therein plenty of desired color components can be collected most effectively. Further, as shown in FIG. 4, if the diameter of the light-receiving end-surface of the fiber optic cable is enlarged to D0, it may be possible to collect visible light containing therein all of its wavelength components.

The optical fiber may be fixed earlier at their light-receiving ends at the corresponding focusing positions of the respective lenses in the solar ray collecting device at the manufacturer's works, or they may be movably fixed in the solar ray collecting device so that the positions of their light-receiving ends can be additionally adjusted by the user in the axial directions of the lenses and according to the colors of the light to be collected.

As is apparent from the foregoing description, according to the present invention, it may be possible to provide a bioassaying device with visible light radiation capable of irradiating a living subject with light by changing its energy intensity and/or color temperature or at fixed values of its energy intensity and/or color temperature and, thereby, it can precisely and effectively perform experiments with living subjects regarding their reactions to light.

I claim:

1. A bioassay device for exposing a living organism to visible light rays to test reaction of the living organism to said light rays, comprising a base plate having a transparent portion; a plurality of column members mounted vertically on said base plate; adjustable plate means mounted on said column members above said base plate; first adjustment means for moving said adjustable plate means vertically on said column members to adjust distance of said adjustable plate means with respect to said base plate; first fiber optic cable means mounted on said adjustable plate means at an inclined angle with respect to said adjustable plate means and including a first light-emitting end for emitting red color component rays of visible light rays and transmitting said red color component rays through said transparent portion of said base plate and onto a living organism arranged under said transparent portion; second fiber optic cable means mounted on said adjustable plate means at an inclined angle with respect to said adjustable plate means and including a second light-emitting end for emitting blue color component rays of visible light rays and transmitting said blue color component rays through said transparent portion and onto said living organism; third fiber optic cable means mounted on said adjustable plate means at an inclined angle with respect to said adjustable plate means and including a third light-emitting end for emitting green color component rays of visible light rays and transmitting said green color component rays through said transparent portion and onto said living organism; said first, second and third light-emitting ends of said fiber optic cable means not emitting infrared rays or ultraviolet rays; second adjustment means for adjusting the inclined angle of each of said fiber optic cable means with respect to said adjustable plate means simultaneously with adjustment of said distance of said adjustable plate means with respect to said base plate, thereby ensuring the transmitting of color component rays through the transparent portion of said base plate when the distance of said adjustable plate means with respect to said base plate is adjusted; color temperature sensor means arranged on said base plate for monitoring color temperature of rays emitted from said first, second and third light-emitting ends of said fiber optic cable means and transmitted onto said living organism; third adjustment means responsive to said color temperature sensor means for controlling the distance of each light-emitting end from the transparent portion of said base plate to thereby control color temperature of rays transmitted onto said living organism; and illumination intensity sensor means arranged on said base plate for monitoring illumination intensity of rays emitted from said first, second and third light-emitting ends of said fiber optic cable means and transmitted onto said living organism, said first adjustment means being responsive to said illumination intensity sensor means for moving said adjustable plate means to adjust distance thereof with respect to said base plate to thereby control illumination intensity of rays transmitted onto said living organism.

2. A bioassay device as in claim 1, further comprising solar ray collecting means for collecting solar rays; and solar ray transmitting means for transmitting collected solar rays from said solar ray collecting means to each of said fiber optic cable means.

3. A bioassay device as in claim 1, further comprising laboratory dish means arranged beneath said base plate and adapted to receive therein said living organism for bioassay.

4. A bioassay device as in claim 1, further comprising fourth fiber optic cable means mounted on said adjustable plate means for emitting white visible light rays and transmitting said white visible light rays through said transparent portion of said base plate and onto said living organism.

5. A bioassay device as in claim 1, further comprising fourth adjustment means for adjusting distance of said base plate from the living organism arranged under said transparent portion of said base plate.

* * * * *